US006554851B1

(12) United States Patent
Palasis et al.

(10) Patent No.: US 6,554,851 B1
(45) Date of Patent: *Apr. 29, 2003

(54) METHODS OF SEALING AN INJECTION SITE

(75) Inventors: Maria Palasis, Wellesley, MA (US); Lucas S. Gordon, Redmond, WA (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/521,473

(22) Filed: Mar. 8, 2000

Related U.S. Application Data

(60) Provisional application No. 60/133,122, filed on May 7, 1999.

(51) Int. Cl.[7] .............................................. A61B 17/08
(52) U.S. Cl. ...................................................... 606/213
(58) Field of Search ........................................ 606/213

(56) References Cited

U.S. PATENT DOCUMENTS

| 4,071,028 A | | 1/1978 | Perkins ................... 128/303.14 |
| RE32,208 E | * | 7/1986 | Mattei et al. ................ 606/213 |
| 4,890,621 A | * | 1/1990 | Kensey ........................ 606/213 |
| 5,415,657 A | | 5/1995 | Taymor-Luria |
| 5,507,744 A | | 4/1996 | Tay et al. |
| 5,575,815 A | | 11/1996 | Slepian et al. .................. 623/1 |
| 5,624,669 A | * | 4/1997 | Leung et al. ............. 424/78.35 |
| 5,632,727 A | | 5/1997 | Tipton et al. .................. 602/47 |
| 5,681,873 A | | 10/1997 | Norton et al. ............... 523/115 |
| 5,717,030 A | | 2/1998 | Dunn et al. .................. 523/111 |
| 5,725,491 A | | 3/1998 | Tipton et al. .................. 602/43 |
| 5,792,469 A | | 8/1998 | Tipton et al. ................ 424/422 |
| 5,888,533 A | | 3/1999 | Dunn .......................... 424/423 |
| 5,895,412 A | | 4/1999 | Tucker ........................ 606/215 |
| 5,900,245 A | | 5/1999 | Sawhney et al. ............ 424/426 |
| 5,945,115 A | | 8/1999 | Dunn et al. .................. 424/422 |
| 5,947,964 A | | 9/1999 | Eggers et al. .................. 606/41 |
| 5,962,006 A | | 10/1999 | Southard et al. ............ 424/426 |
| 5,964,727 A | | 10/1999 | Edwards et al. .............. 604/22 |
| 5,990,194 A | | 11/1999 | Dunn et al. .................. 523/113 |
| 6,159,232 A | * | 12/2000 | Nowakowski et al. ...... 606/213 |
| 6,391,048 B1 | | 5/2002 | Ginn et al. |

* cited by examiner

Primary Examiner—Gary Jackson
(74) Attorney, Agent, or Firm—Kenyon & Kenyon

(57) ABSTRACT

Methods of sealing an injection site of a tissue are provided, where therapeutic agent has been injected into tissue, resulting in increased efficiency or agent uptake. Also provided are methods for delivering therapeutic agent to a tissue, which include injecting a therapeutic agent into a tissue and subsequently sealing the injection site, or engaging an injection device with the tissue for a sufficient period of time that sealing is not necessary to avoid leakage of the therapeutic agent. In one embodiment radio frequency cautery is used to seal the injection site upon needle removal from the tissue. In other embodiments, the injection site is sealed by resistance heating, laser heating or plugging the site with a solid plug or coagulating material at the site.

5 Claims, No Drawings

METHODS OF SEALING AN INJECTION SITE

The present application claims the benefit of U.S. Provisional Application No. 60/133,122, filed May 7, 1999.

FIELD OF THE INVENTION

The present invention relates to methods of sealing an injection site, where therapeutic agent has been injected into tissue resulting in increased efficiency or agent uptake. The present invention also relates to methods for delivering therapeutic agent to a tissue, which include injecting a therapeutic agent into a tissue and subsequently sealing the injection site, or engaging an injection device with the tissue for a sufficient period of time that sealing is not necessary to avoid leakage of the therapeutic agent.

BACKGROUND OF THE INVENTION

The treatment of disease such as vascular disease by local pharmacotherapy presents a means of delivering therapeutic drug doses to target tissues while minimizing systemic side effects. Such localized delivery of therapeutic agents has been proposed or achieved using medical devices such as catheters, needle devices and various coated implantable devices such as stents.

The localized delivery of therapeutic agents using needle devices has the advantages of precise placement and accurate control over the volume and rate of delivery. The processing mechanisms by which therapeutic agent is released from the needle and absorbed by surrounding tissue, however, is not well-characterized.

SUMMARY OF THE INVENTION

In one embodiment, the invention includes a method of sealing an injection site by performing radio frequency cautery at the mouth of a needle track in tissue in order to seal the mouth of the needle track. The needle track is formed in tissue after a therapeutic agent has been injected into a tissue with an injection device and subsequently removed from the tissue.

In other embodiments the mouth of a needle track in tissue is sealed by performing resistance heating at the mouth, performing laser heating at the mouth, plugging the mouth with a solid plug, and coagulating material at the mouth of the needle track.

In another embodiment, the invention includes a method of delivering therapeutic agent to tissue by injecting the therapeutic agent into the tissue of a mammal with an injection device, where the injection device is kept engaged with the tissue for a sufficient period of time after the injection has been completed to prevent the therapeutic agent from leaking from the injection site.

In other embodiments, the invention includes methods of delivering therapeutic agent to tissue, wherein a thickening agent, bioadhesive material or tissue sealant is added to the materials being delivered to reduce or eliminate dispersion or leakage of the therapeutic agent from the tissue after injection into the tissue. The therapeutic agent is delivered by injecting the therapeutic agent into tissue, preferably by an injection needle.

In another embodiment, the invention includes a method for delivering a therapeutic agent into a tissue in a mammal, which includes injecting a therapeutic agent into tissue with an injection needle, withdrawing the injection needle from the tissue, thus forming a needle track having a mouth in the tissue, and sealing the mouth of said needle track. Preferably, the mouth of the needle track is sealed by radio frequency cautery. In other embodiments, the mouth of the needle track is sealed by resistance heating, laser heating, plugging the mouth with a solid plug, or by coagulating a material at the mouth of the needle track.

DETAILED DESCRIPTION

The inventors have surprisingly found that when therapeutic agent is delivered to target tissue with an injection device such as a needle, leaking and dispersion often result upon removal of the device from the tissue. For example, the inventors have discovered that where an injection is performed via a needle, there is potential for leakage of the administered therapeutic agent along the needle track left by needle withdrawal. This problem is exacerbated in situations where the therapeutic agent is injected into the tissue of an organ that undergoes expansion and contraction, such as the heart. In such cases, the organ wall thins during organ expansion, thus facilitating the leakage of previously-injected therapeutic agent from the organ tissue through the needle track and thereby decreasing the actual dose of therapeutic agent delivered to the target site and increasing systemic distribution of the drug.

The problem of leakage of injected therapeutic agent has not previously been appreciated. Conventionally, injection devices are immediately withdrawn from target tissue following injection without safeguards for the possibility of leakage because it has been assumed, given the relatively small volume of therapeutic agent that is administered by injection, that the therapeutic agent is immediately absorbed by the target tissue.

The present invention solves the problems discovered by the inventors by providing any suitable means for inhibiting loss of injected therapeutic agent prior to cell uptake. Embodiments of the invention thus result in an increased exposure of the target tissue to the therapeutic agents administered, and thus, increased efficiency of localized drug delivery. Other embodiments of the invention include sealing the mouth of the needle track (at the injection site) upon needle removal. The methods of the invention have the additional benefit of permitting a relatively large volume of therapeutic agent to be effectively and efficiently administered. Examples of injection volumes of the present invention include a range of about 1 $\mu$l to about 1 ml, preferably 10–100 $\mu$l.

The invention is described herein with specific reference to an injection needle as the delivery device. Examples of specific devices incorporating injection needles, and thus within the scope of the invention, include needle injection catheters, hypodermic needles, biopsy needles, ablation catheters, cannulas and any other type of medically useful needle. It will be understood by one of ordinary skill in the art that other injection devices are contemplated and are within the scope of the invention. Specifically, any device competent to penetrate tissue is contemplated, particularly those that create an opening through which a delivered agent may escape or "leak out." Non-needle injection devices are also contemplated by the present invention. Examples of non-needle injection devices include, but are not limited to, transmural myocardial revascularization (TMR) devices and percutaneous myocardial revascularization (PMR) devices or any other device capable of wounding or creating a channel or crater in tissue. Further examples of suitable injection devices include ablation devices and needle-free injectors which propel fluid using a spring or pressurized gas, such as carbon dioxide injection devices.

In one embodiment of the present invention, therapeutic agent is delivered to tissue by injecting the therapeutic agent into tissue via an injection device, preferably an injection needle. Following injection, the injection needle may be kept engaged with the tissue (i.e., the needle is not withdrawn) for a period of time after the injection has been completed. The time period that the needle is kept engaged with the tissue is sufficient for the therapeutic agent to be substantially completely absorbed by the target tissue and may include a prolonged time period. Preferably, this time period is within the range of about 5 seconds to about 2 minutes; more preferably, the time period is within the range of about 5 seconds to about 30 seconds. When the needle is subsequently withdrawn, leakage of the therapeutic agent is minimized or eliminated because it has already been absorbed by the target tissue.

In another embodiment, therapeutic agent is delivered to tissue by injecting therapeutic agent into tissue with an injection needle, wherein a thickening agent is added to the therapeutic agent prior to injection. As used herein, "thickening agent" refers to any biocompatible additive that results in an increased viscosity of the materials being injected. By way of example, suitable thickening agents include albumin, iohexol or other contrast agent, alginates, polyacrylic acid, hyaluronic acid, dextran, collagen, gelatin, polyethylene glycol, poloxamers and various biocompatible polymers.

Suitable biocompatible polymers for use in the present invention are hydrophilic or hydrophobic, and include, but are not limited to, polycarboxylic acids, cellulosic polymers, including cellulose acetate and cellulose nitrate, gelatin, polyvinylpyrrolidone, cross-linked polyvinylpyrrolidone, hydrogels, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, ethylene vinylacetate, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers.

By adding a thickening agent, the therapeutic agent has an increased ability to resist forces tending to push the therapeutic agent out of the tissue via the needle tracks. Preferably in this embodiment, the injection needle remains engaged with the tissue for a period of time sufficient to allow cellular uptake of substantially all of the therapeutic agent. In an even more preferred embodiment, the combination of therapeutic agent and thickening agent is sufficient to inhibit any leaking of the therapeutic agent from the tissue when the delivery device is withdrawn from the tissue.

In another embodiment, therapeutic agent is delivered to tissue by injecting therapeutic agent into tissue with an injection needle, wherein a bioadhesive material is added to the materials being injected. As used herein, "bioadhesive material" refers to any biocompatible additive that results in an increase of the affinity of the injected material for tissue. Bioadhesive materials for use in conjunction with the invention include suitable bioadhesive materials known to those of ordinary skill in the art. By way of example, suitable bioadhesive materials include fibrinogen with or without thrombin, fibrin, fibropectin, elastin, laminin, cyanoacrylates, polyacrylic acid, polystyrene, bioabsorbable and biostable polymers derivatized with sticky molecules such as arginine, glycine, and aspartic acid, and copolymers.

Preferably in this embodiment, the injection needle remains engaged with the tissue for a period of time sufficient to allow cellular uptake of substantially all of the therapeutic agent. In an even more preferred embodiment, the combination of therapeutic agent and bioadhesive material is sufficient to inhibit any leaking of the therapeutic agent from the tissue when the delivery device is withdrawn from the tissue.

In another embodiment, therapeutic agent is delivered to tissue by injecting the therapeutic agent into the tissue with an injection needle, wherein a tissue sealant is used to seal the mouth of the needle track upon needle removal. The sealant is delivered to the mouth of the needle track by any suitable means, such as through a lumen of a multi-lumen catheter, in which case the injection needle is delivered via a separate lumen. Alternatively, for example, the sealant may be added to the material being injected, or may be coated onto the exterior of the needle. Tissue sealants for use in conjunction with the invention include suitable sealants known to those of ordinary skill in the art. Such tissue sealants preferably include those having suitable bonding properties, elasticity and biodegradability for the tissue to which the sealant is to be applied. By way of example, suitable sealants include cyanoacrylates, collagen, fibrinogen with or without thrombin, fibrin, fibrin glue, fibropectin, elastin, laminin, cyano-acrylates, polyacrylic acid, polystyrene, bioabsorbable and biostable polymers derivatized with sticky molecules such as arginine, glycine, and aspartic acid, and copolymers.

Preferably in this embodiment, the injection needle remains engaged with the tissue for a period of time sufficient to allow cellular uptake of substantially all of the therapeutic agent. In an even more preferred embodiment, the combination of therapeutic agent and tissue sealant is sufficient to inhibit any leaking of the therapeutic agent from the tissue when the delivery device is withdrawn from the tissue.

The invention also includes a method of sealing an injection site at the mouth of a needle track in tissue. A needle track is formed in tissue after a therapeutic agent has been injected into a tissue with an injection device and subsequently removed from the tissue.

According to a preferred embodiment, one method of sealing the injection site is by performing radio frequency cautery at the mouth of the needle track to seal the mouth upon needle removal from the tissue. Cauterization involves using such intense heat to seal the open ends of the tissue. Radio frequency cautery may be performed by any suitable method. Such methods are known to those skilled in the art.

According to another preferred embodiment, a method for sealing the injection site is by resistance heating at the mouth of the needle track. Intense heat may be used to seal the mouth of the needle track upon needle removal. Intense heat used to seal open ends of tissue may be generated by a variety of different methods. In a preferred embodiment, intense heat is generated by resistance heating a metallic probe, such that the generated heat is intense enough to seal the open ends of tissue. Methods of delivering intense heat, and more preferably resistance heating, are known to those skilled in the art.

Another preferred embodiment includes a method for sealing the injection site by performing laser heating at the mouth of the needle track to seal the mouth upon needle removal. In this embodiment, laser emitted optical energy may be used to heat biological tissue to a degree suitable for denaturing the tissue proteins such that the collagenous elements of the tissue form a "biological glue" to seal the tissue. Suitable methods of laser heating a tissue are known to those skilled in the art.

According to yet another preferred embodiment, the present invention includes a method for sealing the injection site by plugging the mouth of a needle track with a solid plug or by coagulating one or more materials at the mouth upon needle removal. Examples of materials that may be used in accordance with this embodiment in order to seal the mouth of the needle track include fibrin glue, cyanoacrylate-based adhesives and the like. Other suitable sealant plugs would be apparent to those in the art based on the present disclosure. In a preferred embodiment, the sealant plug may be heated (or cooled, depending on the temperature at which the material being used is liquid) prior to application to the mouth of the needle track, and subsequent cooling (or heating) may aid in solidifying and sealing the tissue. For example, a temperature sensitive polymer, which is liquid at above or below physiological temperature (i.e. about 37° C.) and solidifies at physiological temperature may be used in this embodiment. Examples of suitable materials for use in this embodiment include N-isoproylacrylamide and certain celluloses.

When the injection site is sealed by a coagulating material, the coagulating material is applied to the mouth of the injection site while the material is in a first fluent state. Then the material is maintained in a position so as to plug the mouth of the injection site under conditions which convert the material in situ into a second less-fluent or essentially non-fluent state. The conversion may be achieved either by changing the environment surrounding the material by the addition or removal of chemicals or energy, or by passive means such as maintaining the material at the normal internal body temperature of a patient. The transition of the state of the material from a fluent state to a less fluent or essentially non-fluent state may be the result of a phase change or of a viscosity change or of polymerization.

Preferably the material is one or more biocompatible materials. In a preferred embodiment the material is a polymeric material, which can be applied as polymers, monomers, macromers or combinations thereof. The polymeric materials are preferably those materials that can be polymerized or have their viscosity altered in vivo, preferably by the application of light, ultrasound, radiation or chelation, alone or in the presence of added catalyst or by a change to physiological pH, diffusion or calcium ions (alginate) or borate ions (polyvinyl alcohol) into the polymer or change in temperature to body temperature.

Examples of polymers that may be suitable for use in this embodiment include those polymers listed above as being suitable thickening agents. Examples of in situ polymerization include, but are not limited to, alginates crosslinked with multivalent cations, fibrinogen crosslinked with thrombin and photochemical crosslinking. Further examples of suitable polymers include the following. Materials which polymerize or alter viscosity as a function of temperature include poly(oxyalkene) polymers and copolymers such as poly(ethylene oxide)-poly(propylene oxide) (PEO-PPO) copolymers, and copolymers and blends of these polymers with polymers such as poly(alpha-hydroxy) acids, including but not limited to lactic, glycolic and hydroxybutyric acids, polycaprolactones, and polyvalerolactones. Examples of materials which polymerize in the presence of divalent ions such as calcium, barium, magnesium, copper, and iron include naturally occurring polymers collagen, fibrin, elastin, agarose, agar, polysaccharides such as hyaluronic acid, hyalobiuronic acid, heparin, cellulose, alginate, curdlan, chitin and chitosan, and derivatives thereof, cellulose acetate, carboxymethyl cellulose, hydroxymethyl cellulose, cellulose sulfate sodium salt, and ethylcellulose. Examples of materials that can be crosslinked photochemically with ultrasound or with radiation generally include those materials that contain a double bond or a triple bond; examples include monomers which are polymerized into poly(acrilic acids), poly(acrylates), polyacrylamides, polyvinyl alcohols, polyethylene glycols, and ethylene vinyl acetates. Examples of materials that can be crosslinked by the addition of covalent crosslinking agents, such as glutaraldehyde, succindialdehyde or carbodiimide, include amino containing polymers including polypeptides and proteins such as albumin and polyethyleneimine.

In an alternative embodiment, a non-polymeric coagulant may be used, wherein the non-polymeric material is capable of transforming into a substantially solid matrix in situ is either added to the therapeutic agent prior to injection or applied to the mouth of a needle track after a needle is removed from tissue.

The non-polymeric material in this embodiment may be combined with at least one organic solvent. Suitable organic solvents are those that are biocompatible, pharmaceutically-acceptable, and will at least partially dissolve the non-polymeric material. The organic solvent has a solubility in water ranging from miscible to dispersible. The solvent is capable of diffusing, dispersing, or leaching from the composition in situ into aqueous tissue fluid of the implant site such as blood serum, lymph, cerebral spinal fluid (CSF), saliva, and the like. Solvents that are useful include, for example, substituted heterocyclic compounds such as N-methyl-2-pyrrolidone (NMP) and 2-pyrrolidone (2-pyrol); esters of carbonic acid and alkyl alcohols such as propylene carbonate, ethylene carbonate and dimethyl carbonate; fatty acids such as acetic acid, lactic acid and heptanoic acid; alkyl esters of mono-, di-, and tricarboxylic acids such as 2-ethyoxyethyl acetate, ethyl acetate, methyl acetate, ethyl lactate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, glyceryl triacetate; alkyl ketones such as acetone and methyl ethyl ketone; ether alcohols such as 2-ethoxyethanol, ethylene glycol dimethyl ether, glycofurol and glycerol formal; alcohols such as ethanol and propanol; polyhydroxy alcohols such as propylene glycol, polyethylene glycol (PEG), glycerin (glycerol), 1,3-butyleneglycol, and isopropylidene glycol; dialkylamides such as dimethylformamide and dimethylacetamide; dimethylsulfoxide (DMSO) and dimethylsulfone; tetrahydrofuran; lactones such as ε-caprolactone and butyrolactone; cyclic alkyl amides such as caprolactam; aromatic amides such as N,N-dimethyl-m-toluamide, and 1-dodecylazacycloheptan-2-one; and the like; and mixtures and combinations thereof. Preferred solvents include N-methyl-2-pyrrolidone, 2-pyrrolidone, dimethylsulfoxide, ethyl lactate, propylene carbonate, glycofurol, glycerol, and isopropylidene glycol. Preferably the organic solvent is biocompatible and non-toxic.

A composition of the non-polymeric material is preferably flowable with a consistency that ranges from watery to slightly viscous to a putty or paste. The non-polymeric material eventually coagulates to a microporous, solid matrix upon the dissipation of the organic solvent into adjacent tissue fluids. The non-polymeric composition can be manipulated and shaped within the defect site as it solidifies. Advantageously, the moldability of the composition as it hardens allows it to conform to irregularities, crevices, cracks, holes, and the like, in the implant site. The resulting substantially solid matrix is preferably biodegradable, bioabsorbable, and/or bioerodible, and will be gradually absorbed into the surrounding tissue fluids, and become disintegrated through enzymatic, chemical and/or cellular hydrolytic action. The term "biodegradable" means that the non-polymeric material and/or matrix of the implant will degrade over time by the action of enzymes, by simple or enzymatically catalyzed hydrolytic action and/or by other similar mechanisms in the human body. The term "bioerodible" means that the implant matrix will erode or degrade over time due, at least in part, to contact with substances found in the surrounding tissue fluids, cellular action, and the like. By "bioabsorbable," it is meant that the non-polymeric matrix will be broken down and absorbed within the human body, for example, by a cell, a tissue, and the like.

Optionally, the composition of non-polymeric material of this embodiment can be combined with a minor amount of a biodegradable, bioabsorbable thermoplastic polymer such as a polylactide, polycaprolactone, polyglycolide, or copolymer thereof, to provide a more coherent solid implant or a composition with greater viscosity so as to hold it in place while it solidifies. The non-polymeric materials are also capable of coagulating or solidifying to form a solid implant matrix upon the dissipation, dispersement or leaching of the solvent component from the composition and contact of the non-polymeric material with an aqueous medium. The solid matrix has a firm consistency ranging from gelatinous to impressionable and moldable, to a hard, dense solid.

Non-polymeric materials according to this embodiment that are suitable for use in the present invention generally include any having the foregoing characteristics. Examples of useful non-polymeric materials include sterols such as cholesterol, stigmasterol, P-sitosterol, and estradiol; cholesteryl esters such as cholesteryl stearate; $C_{12}$–$C_{24}$ fatty acids such as lauric acid, myristic acid, palmitic acid, stearic acid, arachidic acid, behenic acid, and lignoceric acid; $C_{18}$–$C_{36}$ mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$–$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; spingomyelins such as stearyl, palmitoyl, and tricosanyl spingomyelins; ceramides such as stearyl and palmitoyl ceramides; glycosphingolipids; lanolin and lanolin alcohols; and combinations and mixtures thereof. Preferred non-polymeric materials include cholesterol, glyceryl monostearate, glycerol tristearate, stearic acid, stearic anhydride, glyceryl monooleate, glyceryl monolinoleate, and acetylated monoglycerides.

The present invention also includes a method for delivering a therapeutic agent into a tissue in a mammal, which includes injecting a therapeutic agent into tissue of a mammal in need of said therapeutic agent, with an injection needle, withdrawing the injection needle from the tissue, thus, forming a needle track in the tissue, and sealing the mouth of the needle track. Preferably, the mouth of the needle track is sealed by radio frequency cautery. In other embodiments, the mouth of the needle track is sealed by resistance heating, laser heating, plugging the mouth with a solid plug, by coagulating a material at the mouth of the needle track or by other methods known to those skilled in the art as described above.

In addition to the above embodiments, other methods of sealing an injection site such as cryogenic techniques and electrosurgical techniques are contemplated by the present invention.

Any of the above-described thickening agents, bioadhesive materials, tissue sealants, solid plugs, or coagulants (including polymeric and non-polymeric coagulants), or compositions containing any of the above, may contain one or more additives that would be known to those in the art.

The term "therapeutic agent" as used herein includes one or more "therapeutic agents" or "drugs". The terms "therapeutic agents" and "drugs" are used interchangeably herein and include pharmaceutically active compounds, nucleic acids with and without carrier vectors such as lipids, compacting agents (such as histones), virus (such as adenovirus, andenoassociated virus, retrovirus, lentivirus and (virus), polymers, hyaluronic acid, proteins, cells and the like, with or without targeting sequences. The injection administered in accordance with the invention includes the therapeutic agent(s) and solutions thereof.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitorfurantoin; anesthetic agents such as lidocaine, bupivacaine, and ropivacaine; nitric oxide (NO) donors such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, antiplatelet receptor antibodies, enoxaparin, hirudin, Warafin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as antiapoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery mediated is formulated as needed to maintain cell function and viability. Any modifications are routinely made by one skilled in the art.

Polynucleotide sequences useful in practice of the invention include DNA or RNA sequences having a therapeutic effect after being taken up by a cell. Examples of therapeutic polynucleotides include antisense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor $\alpha$ and $\beta$, platelet-derived endothelial growth factor, platelet-derived growth factor, tumor necrosis factor $\alpha$, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Organs and tissues that may be treated by the methods of the present invention include any mammalian tissue or organ, whether injected in vivo or ex vivo. Non-limiting examples include heart, lung, brain, liver, skeletal muscle, smooth muscle, kidney, bladder, intestines, stomach, pancreas, ovary, prostate, eye, tumors, cartilage and bone.

The therapeutic agents can be used, for example, in any application for treating, preventing, or otherwise affecting the course of a disease or tissue or organ dysfunction. For example, the methods of the invention can be used to induce or inhibit angiogenesis, as desired, to prevent or treat restenosis, to treat a cardiomyopathy or other dysfunction of the heart, for treating Parkinson's disease or a stroke or other dysfunction of the brain, for treating cystic fibrosis or other dysfunction of the lung, for treating or inhibiting malignant cell proliferation, for treating any malignancy, and for inducing nerve, blood vessel or tissue regeneration in a particular tissue or organ.

Therapeutic agents may be directly injected into tissue, or may be delivered in a solution or other form and may be delivered via a carrier. Therapeutic agents may be delivered via microspheres that are injected into the tissue, rather than injecting therapeutic agents directly into the tissue. In a preferred embodiment, therapeutic agents may be injected via microspheres into muscle tissue. Injecting therapeutic agents via microspheres may result in sustained release or delivery of the drug. Direct injection of therapeutic agents may represent an effective means to treat the entire myocardium. The authors have found that injected agents tend to disperse throughout the myocardium into uninjected areas. Thus, the number of injections that is necessary in order to deliver therapeutic agents to a specific area of tissue may be decreased.

In a preferred embodiment, therapeutic agents are delivered to muscle tissue by injecting a solution of microspheres directly into the muscle tissue. In a more preferred embodiment, the muscle tissue is the heart.

EXAMPLE

The myocardium of a mammal was treated by injecting therapeutic agents into muscle tissue. Upon injection of a gene, with and without a viral vector, protein expression is limited to the immediate area where the injections were made. Applicants surprisingly found that upon injection of a solution of microspheres directly into muscle tissue, the microspheres became dispersed throughout the myocardium and away from the injection site. Single 10–100 $\mu$l (in volume) injections of a solution of microspheres were made into the anterior, lateral and posterior wall of the left ventrical, resulting in 1–6% of the injectate being recovered in the uninjected septal wall and 0.1–1% of the injectate being recovered in the uninjected right ventrical.

This data shows that an injected solution of microspheres spreads significantly beyond the site of injection and thus, delivers therapeutic agent beyond the site of the injection. In this manner, it may be possible to treat a significant portion of the heart with a therapeutic protein or drug via a limited number of injections into the muscle tissue.

Furthermore, it may be possible to modulate the dispersion of therapeutic agents in the heart by adding ligand to the therapeutic agents, which may bind to cell surface receptors, extracellular matrix components or other components of the myocardial tissue.

What is claimed is:

1. A method of inhibiting leakage of a therapeutic agent that has been injected into a target tissue comprising:

injecting the therapeutic agent into the target tissue with an injection device;

removing the injection device from the target tissue, wherein a track is created in the tissue upon removal of the injection device; and applying a coagulating material at the mouth of the track to seal the mouth and to inhibit leakage of the therapeutic agent from the mouth.

2. The method of claim 1, wherein the coagulating material is a polymeric material or a monomeric material that is polymerized into a polymeric material.

3. The method of claim 2, wherein said polymeric material is selected from the group consisting of poly(oxyalkene) polymers and copolymers and blends with poly(alphahydroxy) acids, collagen, elastin, agarose, agar, hyaluronic acid, hyalobiuronic acid, heparin, cellulose, alginate, curdlan, chitin, chitosan, and derivatives thereof, cellulose acetate, carboxymethyl cellulose, hydroxymethyl cellulose, cellulose sulfate sodium salt, ethylcellulose, poly(acrilic acids), poly(acrylates), polyacrylamides, polyvinyl alcohols, polyethylene glycols, ethylene vinyl acetates, and amino containing polymers.

4. The method of claim 1, wherein the coagulating material is a non-polymeric material.

5. The method of claim 4, wherein the non-polymeric material is selected from the group consisting of sterols, cholesteryl esters, $C_{12}$–$C_{14}$ fatty acids, $C_{18}$–$C_3$, mono-, di- and triacylglyciderides, sucrose fatty acid esters, sorbitan fatty acid esters, $C_{16}$–$C_{18}$ fatty alcohols, esters of fatty alcohols, esters of fatty acids, anhydrides of fatty acids, phospholipids, sphingosine, spingomyelins, ceramides, glycosphingolipids, lanolin, lanolin alcohols, and derivatives, combinations, and mixtures thereof.

* * * * *

UNITED STATES PATENT AND TRADEMARK OFFICE
CERTIFICATE OF CORRECTION

PATENT NO. : 6,554,851 B1
APPLICATION NO. : 09/521473
DATED : April 29, 2003
INVENTOR(S) : Palasis et al.

It is certified that error appears in the above-identified patent and that said Letters Patent is hereby corrected as shown below:

Column 5, line 24, "N-isoproylacrylamide" should be changed to --N-isopropylacrylamide--;

column 7, line 58, "spingomyelins" should be changed to --sphingomyelins--;

column 7, line 59, "spingomyelins" should be changed to --sphingomyelins--;

column 8, line 45-46, "viral, liposomes" should be changed to --viral liposomes--;

column 9, line 3, "nitorfurantoin" should be changed to --nitrofurantoin--;

column 9, line 5, "lisidomine" should be changed to --linsidomine--;

column 9, line 11, "Warafin" should be changed to --warfarin--;

column 10, line 9, "DNA's" should be changed to --DNAs--;

claim 3, line 8-9 (column 12, line 6-7), "poly(acrilic acids)" should be changed to --poly(acrylic acids)--;

claim 5, line 3 (column 12, line 14), "C18 - C3" should be changed to --C18 - C36--; and claim 5, line 7 (column 12, line 18), "spingomyelins" should be changed to --sphingomyelins--.

Signed and Sealed this

Fifth Day of February, 2008

JON W. DUDAS
*Director of the United States Patent and Trademark Office*